(12) United States Patent
Dikstein

(10) Patent No.: US 10,183,076 B2
(45) Date of Patent: Jan. 22, 2019

(54) TOPICAL COMPOSITIONS FOR TREATMENT OF IRRITATION OF MUCOUS MEMBRANES

(71) Applicant: RESDEVCO RESEARCH AND DEVELOPMENT CO. LTD., Jerusalem (IL)

(72) Inventor: Shabtay Dikstein, Jerusalem (IL)

(73) Assignee: RESDEVCO RESEARCH AND DEVELOPMENT CO. L, Jerusalem (IL)

( * ) Notice: Subject to any disclaimer, the term of this patent is extended or adjusted under 35 U.S.C. 154(b) by 0 days.

(21) Appl. No.: 15/286,578

(22) Filed: Oct. 6, 2016

(65) Prior Publication Data

US 2017/0021023 A1    Jan. 26, 2017

Related U.S. Application Data

(63) Continuation-in-part of application No. 11/914,429, filed as application No. PCT/IL2006/000537 on May 7, 2006, now abandoned.

(30) Foreign Application Priority Data

May 16, 2005    (IL) .......................................... 168603

(51) Int. Cl.
| | | |
|---|---|---|
| *A61K 47/10* | (2017.01) | |
| *A61K 9/00* | (2006.01) | |
| *A61K 47/26* | (2006.01) | |
| *A61K 47/38* | (2006.01) | |
| *A61K 47/14* | (2017.01) | |
| *A61K 47/18* | (2017.01) | |
| *A61K 9/06* | (2006.01) | |
| *A61K 8/00* | (2006.01) | |

(52) U.S. Cl.
CPC ................ *A61K 47/10* (2013.01); *A61K 8/00* (2013.01); *A61K 9/0014* (2013.01); *A61K 9/0034* (2013.01); *A61K 9/0043* (2013.01); *A61K 9/0048* (2013.01); *A61K 9/06* (2013.01); *A61K 47/14* (2013.01); *A61K 47/183* (2013.01); *A61K 47/186* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,106,615 A | 4/1992 | Dikstein | |
| 5,376,365 A * | 12/1994 | Dikstein | ............... A61K 9/0043 424/78.02 |
| 6,238,648 B1 | 5/2001 | Leusch | |
| 6,414,035 B1 | 7/2002 | Vargas Munita et al. | |
| 6,685,918 B1 | 2/2004 | Wills et al. | |
| 6,890,961 B2 | 5/2005 | Li et al. | |
| 7,198,779 B2 | 4/2007 | Rifa Piñol et al. | |
| 7,619,008 B2 | 11/2009 | Yang et al. | |
| 2002/0022668 A1 * | 2/2002 | Welsh | .................. A61K 31/045 514/738 |
| 2003/0149100 A1 | 8/2003 | Li et al. | |
| 2004/0247532 A1 | 12/2004 | Pinol et al. | |

FOREIGN PATENT DOCUMENTS

| | | |
|---|---|---|
| CA | 2366627 A1 | 9/2000 |
| CA | 2481394 A1 | 12/2003 |
| DE | 3734835 A1 | 6/1988 |
| EP | 1035844 A1 | 9/2000 |
| EP | 1354580 A1 | 10/2003 |
| JP | 2004051545 A | 2/2004 |
| JP | 2005104966 A | 4/2005 |
| WO | 1999/027922 A1 | 6/1999 |
| WO | 2001/037796 A1 | 5/2001 |
| WO | 2002/049615 A2 | 6/2002 |
| WO | 2003/028699 A1 | 4/2003 |
| WO | 2003/066025 A1 | 8/2003 |
| WO | 2003/099258 A1 | 12/2003 |
| WO | 2006/123324 A1 | 11/2006 |

OTHER PUBLICATIONS

International Search Report for PCT/IL2006/000537, dated Oct. 10, 2006.
Written Opinion of the International Search Authority for PCT/IL2006/000537, dated Oct. 10, 2006.
International Preliminary Report on Patentability Chapter II for PCT/IL2006/000537, dated Sep. 24, 2007.
Written Opinion of the International Preliminary Examining Authority for PCT/IL2006/000537, dated Jul. 18, 2007.
Database CA [online] Chemical Abstracts Service, Columbus, Ohio, US; Iwao, Junichi et al: "Allergy-inhibiting ophthalmic solutions containing cyproheptadine or its salts", XP002398971, retrieved from STN Database accession No. 111:63983.
Database CA [online] Chemical Abstracts Service, Columbus, Ohio, US; Morita, Takakazu et al: "Stable pirenoxine ophthalmic solutions", XP002398972, retrieved from STN Database accession No. 113:46324.

(Continued)

*Primary Examiner* — Jeffrey S Lundgren
*Assistant Examiner* — Meghan Finn

(57) ABSTRACT

A topical pharmaceutical or cosmetic composition for treatment of irritation of mucous cells such as mucosal cells of the eye, nose, and vagina is disclosed. The composition comprises an aqueous solution of at least one polyol selected from the group consisting of xylitol, myoinositol and mannitol and at least one substance selected from the group consisting of glycerol and urea. The composition contains less than 0.01% inorganic salt and is free of any oil-in-water or wax-in-water emulsion. In particularly preferred embodiments, the composition comprises an aqueous solution containing 1.5-5% (w/v) xylitol and 0.9-2.0% (w/v) glycerol.

3 Claims, No Drawings

(56) References Cited

OTHER PUBLICATIONS

Follmann, P. Szemészet vol. 141, 2004, pp. 305-308.
Fang et al., "Ability if Electrical Measurements to Predict Skin Moisturization", J. Cosmet. Sci. 52, 23-33, Jan./Feb. 2001.
Notice of Opposition dated May 23, 2013, for European Patent Application No. 06728329.1—English Translation.
Notification concerning Informal Communications with the Applicant for PCT/IL2006/000537, dated Sep. 24, 2007.
Ghosh et al., "The Role of Sodium Dodecyl Sulfate (SDS) Micelles in Inducing Skin Barrier Perturbation in the Presence of Glycerol", J. Cosmet. Sci., 58, 109-133, Mar./Apr. 2007.
Response to PCT International Search Report and Written Opinion of ISA for PCT/IL2006/000537, dated Oct. 10, 2006.
Response to Written Opinion of IPEA for PCT/IL2006/000537, dated Jul. 18, 2007.
Sagiv et al., "A Novel in Vivo Model in Guinea Pigs for Dry Skin Syndrome", Skin Research and Technology 2000, vol. 6, pp. 37-42.

\* cited by examiner

TOPICAL COMPOSITIONS FOR TREATMENT OF IRRITATION OF MUCOUS MEMBRANES

REFERENCE TO RELATED APPLICATIONS

This application is a Continuation-in-Part of U.S. patent application Ser. No. 11/914,429, filed Nov. 14, 2007, which is a national phase filing under 35 U.S.C. 371 of International (PCT) Application No. PCT/IL2006/000537, filed May 7, 2006, and which claims priority from Israel Patent Application No. 168603, filed May 16, 2005, all of which are hereby incorporated by reference in their entirety.

FIELD AND BACKGROUND OF THE INVENTION

The present invention provides a new combination of topically active substances, for the prevention and alleviation of cell damage, caused by preservatives, detergents or drugs, used in topical pharmaceutical, cosmetic or veterinary compositions.

Many substances are applied topically to the skin or mucous membranes of humans or animals in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, topical respiratory agents, ocular drugs such as eyedrops and saline solutions, therapeutic retinoids, anti-dandruff agents, external analgesics such as capsaicin products, topical contraceptives, topical drug delivery systems, gastrointestinal agents such as suppositories, enemas and hemorrhoid treatments, reproductive system agents such as vaginal treatments, oral treatments such as lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases, topical products contain chemicals which may produce "irritation," including various inflammation symptoms or signs, when applied to the skin or mucosa. The present invention is directed to compositions for inhibiting the irritation associated with such topical products.

The occurrence, frequency and nature of topical-product-induced irritation often vary from user to user. The severity of irritation to the susceptible user may range from subclinical to mild to severe. Typical symptoms of "irritation" include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. antigens).

Many ingredients used in topical products are known irritants or are potentially irritating, especially to people with "sensitive skin." These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to designate a product's reduced tendency to cause irritation in consumers with sensitive skin. Many skin and mucosal irritation responses, however, are not allergic in origin. In any event, it is often not feasible or practical to identify or eliminate all of the irritating chemical(s), particularly when the irritating chemical(s) are the active ingredient of the product or are required for formulation, preservative or other functional reasons.

U.S. Pat. No. 6,414,035 discloses that oral administration of a polyol such as xylitol can increase the effectiveness of drugs that treat yeast infections affecting mucosal tissue such as the eyes, the mouth, the urinary tract, and the vagina. The daily dose of the polyol is on the order of 0.1-1 g/kg body weight. The inventors state that higher doses can be administered for limited periods of time, as high doses of orally administered xylitol can lead to side effects such as diahrrea.

U.S. Pat. No. 7,619,008 discloses the use of xylitol for treatment of vaginal infections. The therapeutic agent is capable of inhibiting and/or killing *Gardnerella*, *Candida*, and/or *Trichomonas* pathogens without significantly inhibiting the growth of Lactobacillus acidophilus. The method of treatment comprises topical application of a composition comprising 0.1%-10% (w/v) of a therapeutic agent that includes xyitol and 0.05%-5% (w/v) of a gelling agent, and is characterized by an osmolarity of 270-310 mOs/L, a pH of between 2.5 and 5.0, and as forming a gel after application.

A composition for topical application of polyols for treatment of irritation of mucosal tissue remains a long-felt, yet unmet need.

SUMMARY OF THE INVENTION

The present invention is designed to meet this long-felt need by providing an effective topical composition comprising polyols that is effective for combating damaging effects of irritants to mucous cells.

It is therefore an object of this invention to provide a topical pharmaceutical or cosmetic composition for treatment of irritation of mucous cells, wherein said composition comprises an aqueous solution of (a) at least one polyol selected from the group consisting of xylitol, myoinositol and mannitol; and (b) at least one substance selected from the group consisting of glycerol and urea; further wherein said composition contains less than 0.01% inorganic salt and is free of any oil-in-water or wax-in-water emulsion.

It is a further object of this invention to provide such a topical pharmaceutical or cosmetic composition for treatment of irritation of mucous cells selected from the group consisting of mucous membrane of the eye, mucous membrane of the nose, and mucous membrane of the vagina.

It is a further object of this invention to provide the topical pharmaceutical or cosmetic composition as defined in any of the above, wherein said at least one polyol is xylitol and said at least one substance selected from the group consisting of glycerol and urea is glycerol. In some preferred embodiments of the invention, wherein said composition comprises 1.5-5% (w/v) xylitol and 0.9-2.0% (w/v) glycerol.

It is a further object of this invention to provide the topical pharmaceutical or cosmetic composition as defined in any of the above, wherein said composition does not contain any antibiotics.

It is a further object of this invention to provide the topical pharmaceutical or cosmetic composition as defined in any of the above, comprising at least one viscosity enhancing agent. In some preferred embodiments of the invention, said composition comprises at least one viscosity enhancing agent in a concentration that yields a viscosity of between 5 and 100 cP. In some especially preferred embodiments of the invention, said viscosity enhancing agent is hydroxypropylcellulose 4000, and further wherein said composition comprises hydoxypropylcellulose 4000 in a concentration of 0.4% (w/v).

It is a further object of this invention to provide the topical pharmaceutical or cosmetic composition as defined in any of the above, comprising at least one pharmaceutically active agent.

It is a further object of this invention to provide the topical pharmaceutical or cosmetic composition as defined in any of the above, comprising at least one substance selected from the group consisting of pharmaceutically acceptable excipients; pharmaceutically acceptable additives; and pharmaceutically acceptable preservatives.

It is a further object of this invention to provide the topical pharmaceutical or cosmetic composition as defined in any of the above, wherein said composition is for treatment of irritation of mucous membranes of the eye. In some preferred embodiments of the invention in which the composition is for treatment of irritation of mucous membranes of the eye, said irritation of mucous membranes of the eye comprises irritation of mucous membranes of the eye caused by at least one cause selected from the group consisting of allergies, chemical pollutants, and physical irritants. In some preferred embodiments of the invention in which the composition is for treatment of irritation of mucous membranes of the eye, the composition comprises 1.4% (w/v) glycerol and 1.9% (w/v) xylitol. In some preferred embodiments of the invention in which the composition is for treatment of irritation of mucous membranes of the eye, the composition consists of 1.4% (w/v) glycerol; 1.9% (w/v) xylitol; 0.3% (w/v) hydroxypropylcellulose 4000; 0.1% (w/v) trisodium citrate dihydrate; 0.01% (w/v) benzalkonium chloride; base to adjust pH to 7.0; and, the balance water.

It is a further object of this invention to provide the topical pharmaceutical or cosmetic composition as defined in any of the above, wherein said composition is for treatment of irritation of mucous membranes of the nose. In some preferred embodiments of the invention in which the composition is for treatment of irritation of mucous membranes of the nose, the composition consists of 1.4% (w/v) glycerol; 3.0% (w/v) xylitol; 0.01% (w/v) alanine; 0.01% (w/v) benzalkonium chloride; and, the balance water.

It is a further object of this invention to provide the topical pharmaceutical or cosmetic composition as defined in any of the above, wherein said composition is for treatment of irritation of mucous membranes of the vagina. In some preferred embodiments of the invention in which the composition is for treatment of irritation of mucous membranes of the vagina, the composition consists of 1.0% (w/v) glycerol; 1.5% (w/v) xylitol; 0.45% (w/v) lactic acid; 0.2% (w/v) methyl paraben; 0.4% (w/v) hydroxypropylcellulose 4000; 0.2% phenylethyl alcohol; and, the balance water.

DETAILED DESCRIPTION OF THE PREFERRED EMBODIMENTS

As used herein, the term "hydroxypropylcellulose 4000" refers to hydroxypropylcellulose of which a 2% aqueous solution has a viscosity of 4000 cP at 25° C. METHOCEL E4MP400 (Dow Chemicals) is an example of a commercially available form of hydroxypropylcellulose 4000.

Unless otherwise stated, all concentrations listed herein are given in percent weight/volume (w/v).

The present invention relates to topical compositions for combating damaging effects of preservatives or other irritants, found, e.g. in multi-dose eye drops, to mucous cells, especially in the conical cells and simultaneously beneficial to those tissues. It was found that glycerol counteracts conical cell damage caused by preservatives such as benzalkonium chloride, cetrimonium bromide, sodium ethylene diamine tetraacetate, etc. Not all the polyhydroxy compounds have such anti-irritant properties. Moreover, it is known that isotonic sodium chloride is toxic to the corneal cells, whereas isotonic glycerol is not toxic. (Follmann, P. et. al. Szeméeszet 141, 305-308, 2004.)

In addition two physicochemical parameters are very important for a good topical composition: increased viscosity and increased spread of the solution.

Increased viscosity is achieved by high molecular weight (equal to more than 0.5 million Dalton) polymers. Increased spread is achieved by surface active agents, however after chronic use the surface active agents usually have damaging effects. (See Animal Studies,a).

It has now been found according to the present invention that all of the above mentioned problems of irritation by preservatives, detergents and other cell damaging agents disappear, and the beneficial effects are preserved or increased, by using a combination of xylitol, myoinositol or mannitol with glycerol and/or urea, preferably together with a surface active agent.

The advantages resulting from the addition of a surface active agent include a decrease in the surface tension of the aqueous solution, thereby increasing the spread. Thus it has now been found, that polysorbate 80 even at a concentration of 0.002% increases the diminished Break Up Time (BUT) in dry eye patients. It is accepted that a BUT of 10 sec. or less indicates dry eye syndrome; see Example 11 below.

Thus, according to the present invention there are now provided topical pharmaceutical or cosmetic compositions for the prevention and treatment of irritation of mucous cells, or skin cells, comprising a combination of:
xylitol, myoinositol or mannitol or any combination of these;
glycerol and/or urea;
water;
in the absence of any oil in water or wax in water emulsion.

The present invention provides topical pharmaceutical or cosmetic compositions for the prevention and treatment of irritation of mucous cells, comprising a combination of:
1.5-5.5% xylitol, myoinositol or mannitol or any combination of these;
0.9-2.0% glycerol;
less than 0.01% inorganic salts;
water;
in the absence of any oil in water or wax in water emulsion.

More specifically the present invention preferably provides a non-irritant topical cosmetic or pharmaceutical composition for mucous cells or for the skin, as defined above, for the prevention of cell damage caused by preservatives, detergents or drugs in topically used cosmetic, pharmaceutical or veterinary compositions.

It is within the scope of the invention wherein the composition of the present invention is intended for use to treatment of irritation of, or prevention of cell damage to, mucous cells. While the invention as disclosed herein is intended in general for use on any type of mucous cell, some specific embodiments are optimized for use with specific types of mucous cells. For example, some embodiments are optimized for use as eye drop compositions. Other embodiments are optimized for use in treatment of irritation of mucosal cells of the vagina. Yet other embodiments are optimized for use in treatment of irritation of mucosal cells of the vagina.

It is well-known that glycerol and xylitol are nearly equally good humectants; see, for example, Cohen, S.; Marcus, Y.; Migron, Y.; Dikstein, S.; Shafran, A. J. Chem. Soc. Faraday Trans. 1993, 89, 3271-3275, which is hereby incorporated in its entirety by reference. It would therefore be expected a priori that a moisturizing composition comprising a mixture of glycerol and xylitol would not be superior to a composition comprising an equivalent amount of one of the two. The current inventor has discovered, surprisingly, that in fact a mixture of glycerol and xylitol treats mucosal tissue more effectively than either one alone; in the case of treatment of nasal mucosal tissue, it was found that a composition containing xylitol and glycerol was significantly more effective than one containing xylitol and glycerol. Examples 12-15 below present experimental evidence for the existence of this unexpected synergistic effect. The observed effect cannot be due to the presence of additional moisturizer, since it is seen even when the effectiveness of a composition comprising isotonic glycerol is compared with the effectiveness of a composition comprising half isotonic glycerol and half isotonic xylitol. Without being bound by theory, it appears that each of the humectants has a different biological effect on the mucosal tissue independent of its moisturizing ability, and that the combination of xylitol and glycerol thereby produces a synergistic effect, and is more effective than either one would be by itself.

In especially preferred embodiments of the present invention there is provided a non-irritant topical cosmetic or pharmaceutical composition for mucous cells or for the skin, as defined above, further comprising at least one pharmaceutically active agent in solution, or in suspension but not in emulsion.

In preferred embodiments of the present invention there is provided a non-irritant topical cosmetic or pharmaceutical composition for mucous cells or for the skin, as defined above, further comprising at least one viscosity enhancing agent.

While the invention will now be described in connection with certain preferred embodiments in the following examples so that aspects thereof may be more fully understood and appreciated, it is not intended to limit the invention of these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of proving what is believed to be the most useful and readily understood description of formulation procedures as well as of the principles and conceptual aspects of the invention. It will be evident to those skilled in the art that the invention is not limited to the details of the following illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

EXAMPLE 1

A moisturizing eye drop composition was prepared according to one preferred embodiment of the present invention. The composition according to this embodiment of the invention comprises, per 100 ml:

| | |
|---|---|
| Sodium hyaluronate | 0.03 g; |
| Povidone | 2.0 g; |
| Glycerol | 1.0 g; |
| Mannitol | 3.2 g; |
| Cetrimide | 0.01 g; |
| NaOH | q.s. to pH 7.0; and, |
| $H_2O$ | to 100 ml. |

EXAMPLE 2

A moisturizing eye drop composition was prepared according to a second preferred embodiment of the present invention. The composition according to this embodiment of the invention comprises, per 100 ml:

| | |
|---|---|
| Glycerol | 1.3 g; |
| Xylitol | 2.2 g; |
| Benzalkonium Chloride | 0.01 g; |
| NaOH | q.s. to pH 7.0; and, |
| $H_2O$ | to 100 ml. |

EXAMPLE 3

A moisturizing eye drop composition was prepared in a unit dose form for single application according to yet another preferred embodiment of the present invention. The composition according to this embodiment of the invention comprises, per 100 ml:

| | |
|---|---|
| Sodium hyaluronate | 0.03 g; |
| Povidone | 2.0 g; |
| Glycerol | 1.0 g; |
| Myoinositol | 3.2 g; |
| NaOH | q.s. to pH 7.0; and, |
| $H_2O$ | to 100 ml. |

EXAMPLE 4

A moisturizing anti-inflammatory eye drop composition was prepared according to yet another preferred embodiment of the present invention. The composition according to this embodiment of the invention comprises, per 100 ml:

| | |
|---|---|
| Glycerol | 1.3 g; |
| Xylitol | 2.2 g; |
| Sodium diclofenac | 0.1 g; |
| Benzalkonium chloride | 0.01 g; |
| NaOH | q.s. to pH 7.2; and, |
| $H_2O$ | to 100 ml. |

EXAMPLE 5

A moisturizing eye drop composition was prepared in a unit dose form for single application according to yet another preferred embodiment of the present invention. The composition according to this embodiment of the invention comprises, per 100 ml:

| | |
|---|---|
| Glycerol | 1.0 g; |
| Mannitol | 1.6 g; |
| Xylitol | 1.6 g; |
| Sodium diclofenac | 0.1 g; |
| NaOH | q.s. to pH 7.2; and, |
| $H_2O$ | to 100 ml. |

EXAMPLE 6

A moisturizing gel for the skin was prepared according to yet another preferred embodiment of the present invention. The composition according to this embodiment of the invention comprises, per 100 ml:

| | |
|---|---|
| Glycerol | 8.0 g; |
| Mannitol | 5.0 g; |
| Urea | 5.0 g; |
| Glycine | 5.0 g; |
| Methylparaben | 0.1 g; |
| Propylparaben | 0.01 g; |
| Polyacrylate 980 adjusted to pH 4.5 | 0.7 g; and, |
| $H_2O$ | to 100 ml. |

EXAMPLE 7

A moisturizing gel for the skin was prepared according to yet another preferred embodiment of the present invention. The composition according to this embodiment of the invention comprises, per 100 ml:

| | |
|---|---|
| Glycerol | 10.0 g; |
| Xylitol | 8.0 g; |
| Urea | 5.0 g; |
| Glycine | 5.0 g; |
| Methylparaben | 0.1 g; |
| Propylparaben | 0.01 g; |
| Polyacrylate 980 adjusted to pH 4.5 | 0.7 g; and, |
| $H_2O$ | to 100 ml. |

EXAMPLE 8

A moisturizing eye drop composition was prepared according to yet another preferred embodiment of the present invention. The composition according to this embodiment of the invention comprises, per 100 ml:

| | |
|---|---|
| Glycerol | 1.4 g (0.5 Osmol); |
| Xylitol | 1.9 g (0.42 Osmol); |
| METHOCEL E4MP400 (viscosity enhancer) | 0.3 g; |
| Trisodium citrate dihydrate (buffer) | 0.1 g; |
| Benzalkonium chloride (preservatve) | 0.01 g (pH 7); |
| $H_2O$ | to 100 ml. |

EXAMPLE 9

A composition for treatment of irritation of mucosal cells of the vagina was prepared according to yet another preferred embodiment of the present invention. The composition according to this embodiment of the invention comprises, per 100 ml:

| | |
|---|---|
| Glycerol | 1.0 g; |
| Xylitol | 1.5 g; |
| METHOCEL E4MP400 (viscosity enhancer) | 0.4 g; |
| Lactic acid (buffer) | 0.45 g; |
| Methyl paraben (preservatve) | 0.02 g; |
| Phenylethyl alcohol (anti-fungal) | 0.2 g; |
| NaOH | q.s. to adjust pH to 4.5; and, |
| $H_2O$ | to 100 ml. |

EXAMPLE 10

A composition for treatment of irritation of nasal mucosal cells was prepared according to yet another preferred embodiment of the present invention. The composition according to this embodiment of the invention comprises, per 100 ml:

| | |
|---|---|
| Glycerol | 1.0 g; |
| Xylitol | 3.0 g; |
| L-alanine (buffer) | 0.01 g; |
| Benzalkonium chloride (preservative) | 0.01 g; |
| H₂O | to 100 ml. |
| The pH of the composition was about 6.2-6.3. | |

EXAMPLE 11

Human studies were performed to demonstrate the effectiveness of the present invention in the treatment of mucosal tissue.

In one study, 23 dry eye patients received in both eyes 1 drop of Fluorescein-Novesin mixture. After 30 seconds the right eye was treated with 1 drop of the composition of the present invention. The patient was asked to blink 2-3 times, then the fluorescein BUT was measured. Afterwards the left eye was treated with 1 drop of a saline solution (0.9% NaCl) having a surface tension of 72 mN/m. The patient was then asked to blink 2-3 times, and the fluorescein BUT was measured.

Treatment=as Control+0.002% Tween 80; surface tension 49 mN/m (dyn/cm)

The results of the study are presented in Table 1.

TABLE 1

| BUT left eye (control) | BUT right eye (treatment) |
|---|---|
| 7.7 ± 0.4 s | 12.7 ± 1.5 s |
| Paired differences 5.0 ± 1.4 sec (p~0.001) | |

EXAMPLE 12

A study was performed of the use of eye drops of the present invention for treatment of conjunctival damage in Dry Eye Syndrome. Patients applied an aqueous solution containing essentially isotonic glycerol to the left eye and a solution containing equal amounts of isotonic glycerol and isotonic xylitol to the right eye. The solutions were applied to the eyes, three times a day over the course of a month.

The results of the study are summarized in Tables 2 and 3.

TABLE 2

| Patient No. | Rose Bengal score (Oxford Scale) | | | |
|---|---|---|---|---|
| | Before | | One month | |
| | R | L | R | L |
| 1 | 3 | 3 | 1 | 2 |
| 2 | 2 | 3 | 0 | 2 |
| 3 | 2 | 3 | 0 | 2 |
| 4 | 3 | 3 | 1 | 2 |
| 5 | 1 | 3 | 1 | 2 |
| mean | 2.2 | 3.0 | 0.6 | 2 |

TABLE 3

| Patient No. | Personal Satisfaction | | | |
|---|---|---|---|---|
| | Before | | One month | |
| | R | L | R | L |
| 1 | 0 | 0 | 2 | 1 |
| 2 | 0 | 0 | 2 | 1 |
| 3 | 0 | 0 | 2 | 1 |
| 4 | 0 | 0 | 2 | 1 |
| 5 | 0 | 0 | 2 | 1 |
| mean | 0 | 0 | 2 | 1 |

0 = not satisfied 1= better 2 = much better

Essentially the same results were obtained by using myoinositol instead of xylitol.

EXAMPLE 13

3 rabbits were treated for 3 months twice daily with eye drops, adjusted to pH 7.0. The average cross section of the epithelial conical cells and the percentage of damaged cells were evaluated by electron microscopy. The results are summarized in Table 4.

TABLE 4

| Treatment | Cross section (μ²) | Damaged cells (%) |
|---|---|---|
| None | 590 | 16 |
| 0.9% NaCl | 542 | 28 |
| 0.01% Benzalkonium Chloride + 0.9% NaCl | 538 | 29 |
| 0.01% Benzalkonium Chloride + 2.5% Glycerol | 699 | 14 |
| 0.01% Cetrimonium Bromide + 0.9% NaCl | 591 | 27 |
| 0.01% Cetrimonium Bromide + 2.5% Glycerol | 625 | 19 |
| 0.1% Na₂ EDTA + 0.9% NaCl | 531 | 15 |
| 0.1% Na₂ EDTA + 2.5% Glycerol | 616 | 17 |
| 0.025% Polysorbate 80 + 0.9% NaCl | 440 | 25 |
| 0.025% Polysorbate 80 + 2.5% Glycerol | 600 | 18 |
| 2.5% Glycerol | 605 | 17 |
| 0.01% Benzalkonium Chloride + 4.5% Xylitol | 554 | 19 |
| 0.01% Benzalkonium Chloride + 5.4% Myoinositol | 584 | 19 |
| 0.01% Benzalkonium Chloride + 5.4% Mannitol | 570 | 21 |

EXAMPLE 14

A preclinical trial was performed in which 10 patients suffering from dry nose syndrome were treated with a composition consisting of an aqueous solution comprising 1% (w/v) glycerol and 3.8% (w/v) mannitol. Each patient's condition was reported as a score in the range of 1-5, where 1 indicates that the treatment did not help at all and 5 indicates a complete absence of symptoms. After 2 weeks of treatment, the average score was 2.95±0.25, and after 4 weeks of treatment, the average score was 2.70±0.25.

EXAMPLE 15

A study was performed in which 34 patients suffering from dry nose syndrome were treated with a composition according to the current invention consisting of an aqueous solution comprising 1% (w/v) glycerol and 3% (w/v) xylitol. Each patient's condition was reported using the same scale given in the preceding example. After 2 weeks, the average score was 4.28±0.13, and after 4 weeks, the average score was 4.50±0.23.

The invention claimed is:

1. A topical pharmaceutical or cosmetic composition for treatment of irritation of a mucous membrane of a nose, wherein said composition consists of:
   1.4% (w/v) glycerol;
   3.0% (w/v) xylitol;
   0.01% (w/v) alanine; and,
   the balance water.

2. A topical pharmaceutical or cosmetic composition for treatment of irritation of a mucous membrane of a nose, wherein said composition consists of:
   1.4% (w/v) glycerol;
   3.0% (w/v) xylitol;
   0.01% (w/v) alanine;
   an effective amount of a pharmaceutically acceptable preservative; and,
   the balance water.

3. The topical pharmaceutical or cosmetic composition according to claim 2, wherein said pharmaceutically acceptable preservative is selected from the group consisting of benzalkonium chloride; methyl paraben; cetrimonium bromide; and, sodium ethylene diamine tetraacetate.

\* \* \* \* \*